United States Patent
Sawyer et al.

(10) Patent No.: US 6,270,782 B1
(45) Date of Patent: Aug. 7, 2001

(54) BODY SPRAY COMPOSITION WITH PEARL-LIKE OIL PHASE DROPLETS IN CONTAINER

(75) Inventors: James Sawyer, Galena; Sandra Steck, Granville; Jane E. Smith, Columbus, all of OH (US)

(73) Assignee: Bath & Body Works, Inc., Reynoldsburg, OH (US)

( * ) Notice: Subject to any disclaimer, the term of this patent is extended or adjusted under 35 U.S.C. 154(b) by 0 days.

(21) Appl. No.: 09/425,702

(22) Filed: Oct. 22, 1999

(51) Int. Cl.[7] .................................. A61K 9/12; A61K 7/48
(52) U.S. Cl. .................................. 424/401; 424/45
(58) Field of Search .................................. 424/400, 401, 424/45; 222/424.5

(56) References Cited

U.S. PATENT DOCUMENTS

| | | |
|---|---|---|
| 2,091,062 | 8/1937 | Yates . |
| 2,331,117 * | 10/1943 | Goodhue et al. . |
| 3,045,872 * | 7/1962 | Hronas et al. . |
| 3,624,208 | 11/1971 | Schmolka . |
| 3,920,883 | 11/1975 | Yamada et al. . |
| 4,083,966 | 4/1978 | Bowell . |
| 4,690,774 | 9/1987 | Vishnupad et al. . |
| 4,767,741 | 8/1988 | Komor et al. . |
| 4,992,476 | 2/1991 | Geria . |
| 4,992,477 | 2/1991 | Geria . |
| 5,023,175 * | 6/1991 | Hosoya et al. . |
| 5,196,187 * | 3/1993 | Nicoll et al. . |
| 5,234,689 | 8/1993 | Lindauer et al. . |
| 5,508,022 | 4/1996 | Clement et al. . |
| 5,599,533 | 2/1997 | Stepniewski et al. . |
| 5,738,839 | 4/1998 | Clement et al. . |
| 5,783,174 * | 7/1998 | Deckner . |
| 5,863,953 | 1/1999 | Lüddecke et al. . |
| 5,871,762 | 2/1999 | Venkitaraman et al. . |
| 5,879,689 | 3/1999 | Date et al. . |
| 5,925,364 | 7/1999 | Ribier et al. . |
| 5,942,216 | 8/1999 | Herb et al. . |

* cited by examiner

*Primary Examiner*—Thurman K. Page
*Assistant Examiner*—P. E. McQueeney
(74) *Attorney, Agent, or Firm*—Colucci & Umans; Peter C. Michalos; Angelo Notaro

(57) ABSTRACT

A body spray assembly includes a container which has an upright position and that is at least partly transparent. A liquid composition in the container is sprayed from the container with a manual spray pump. The composition has an oil phase, an aqueous phase and pigment in the form of particles which are effective to form the oil phase into stable droplets that remain in a droplet layer in the aqueous phase after the composition is allowed to stand for a period of time. The droplets are at least partly visible in the container. The spray pump is free of any plastic parts that extend into the droplet layer when the container is in its upright position to avoid rupturing the stable droplets by contact with these parts. The oil phase contains substantially pure fragrance which is free of solubilizer so that the formation of pearls can occur in the container and does not cloud the aqueous phase.

22 Claims, 2 Drawing Sheets

BODY SPRAY COMPOSITION WITH PEARL-LIKE OIL PHASE DROPLETS IN CONTAINER

FIELD AND BACKGROUND OF THE INVENTION

The present invention relates in general to body sprays and in particular, to a new and useful body spray assembly which comprises a container with a liquid composition having an oil phase in the form of stable droplets which look like pearls or the like.

U.S. Pat. No. 3,920,883, entitled LIQUID COSMETIC COMPOSITION OF A TWO-PHASE TYPE, assigned to Shiseido Co., Ltd., discloses a cosmetic composition containing an oil phase in the form of a dispersion of spheres or droplets, in a homogeneous mixture of organic liquid and water. This patent (the Shisheido patent), which is incorporated here by reference, utilizes finely divided solid particles in the liquid composition to enhance the appearance of the composition in which the oil spheres are transparent, translucent or pearl-like in appearance.

U.S. Pat. No. 4,767,741, entitled TWO-PHASE LIQUID COSMETIC AND METHOD OF PREPARING SAME, which is also incorporated here by reference, discloses a two-phase liquid composition which also contains a dispersion of oil phase spheres or droplets in an organic liquid and water phase to produce a cosmetic having an aesthetically desirable appearance.

This patent also utilizes finely divided solid particles. These particles are the result of precipitated salts in the composition.

A moisturizing composition containing "pearls" of oil droplets is also available from Yves Rosher and is known as BODY THERAPY WITH SAGE & MINT. This product is provided in a glass bottle having a stopper and is shaken before using to disperse the oil droplets into the rest of the liquid composition. The Shiseido patent also advocates the shaking of the cosmetic composition before use for dispersing the oil spheres or droplets into the organic liquid and water phase of the composition.

SUMMARY OF THE INVENTION

An object of the present invention is to provide a body spray which includes fragrance and a moisturizer or other active ingredients, in an attractive assembly comprising a partially or completely transparent container having a spray mechanism for spraying the contents of the container, the contents of the container comprising a composition with a water phase and an oil phase, the oil phase being a dispersion of stable oil droplets or spheres which have a pearl-like appearance and lie in a layer in the composition. Although the preferred embodiment of the invention utilizes oil droplets or spheres which are heavier than the liquid phase and thus form the layer at the bottom of the container, the invention includes compositions which have oil phase droplets that are lighter than the water phase and, thus exists in a layer at the top of the composition.

The composition includes a dispersion of finely divided particles in the form of one or more pigments that the inventors believe contribute to the formation of the stable droplets and which give the droplets a translucent or transparent pearl-like appearance.

Surprisingly, the inventors have found that if certain plastics come into contact with the droplet layer, the droplets are broken, deformed or cling to the plastic parts in sheets or other adverse effects occur. This substantially deteriorates the attractive pearl-like appearance of the droplets and the general appearance of the assembly.

Since an object of the present invention is to provide a composition which can be sprayed, another feature of the invention is to utilize a spray mechanism, which is preferably manual but which may also comprise pressurized aerosol technology, but which has no parts made of the type of plastic which deforms or damages the droplets, near the droplet layer.

Another surprising feature of the invention is that fragrance, which is free of solubilizers must be utilized to form and maintain the pearls, while at the same time avoiding clouding of the aqueous phase. In this way, a substantially crystal clear aqueous phase and a distinct pearl-like droplet layer is produced. Fragrance in the composition will reside in the oil phase due to its lipophilic nature. Solubilizers in the fragrance will impart a hydrophilic nature to fragrance which will adversely effect formation of pearls.

A reservoir pump is used according to the present invention since it does not include a dip tube which extends into the composition. This, both, maintains the stable dispersion of oil phase droplets and produces an attractive container with substantially clear color or colorless liquid above the droplet layer and no unsightly dip tube.

Accordingly, a further object of the invention is to provide a body spray assembly comprising a container which has an upright position and that is at least partly transparent, a liquid composition in the container and spray means connected to the container for spraying the liquid composition from the container. The composition includes an oil phase, an aqueous phase and pigment in the form of particles which are effective to form the oil phase into stable droplets that remain in a droplet layer in the aqueous phase after the composition is allowed to stand for a period of time, the droplets being at least partly visible in the container. The spray means is free of any plastic parts that extend into the droplet layer when the container is in its upright position to avoid rupturing the stable droplets by contact with any plastic parts.

A further object of the present invention is to provide a body spray assembly comprising a container which has an upright position and that is at least partly transparent, a liquid composition in the container and spray means connected to the container for spraying the liquid composition from the container, and the composition including an oil phase, an aqueous phase and pigment in the form of particles which are effective to form the oil phase into stable droplets that remain in a droplet layer in the aqueous phase after the composition is allowed to stand for a period of time, droplets being at least partly visible in the container, the oil phase containing substantially pure fragrance which is free of solubilizer so that the formation of pearls occur in the container and does not cloud the aqueous phase.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
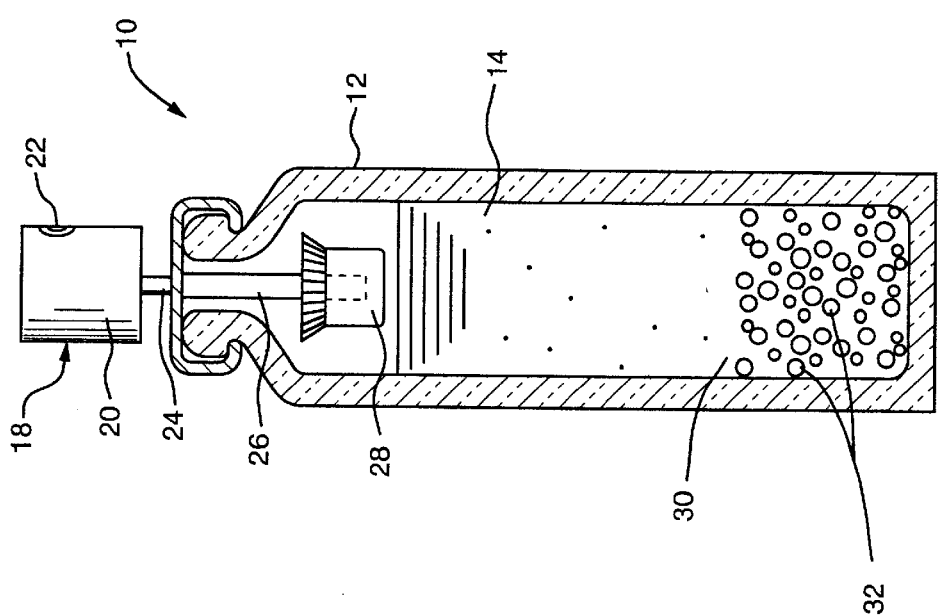
FIG. 1 is a side elevational view of a body spray assembly according to the present invention with an aqueous phase and an oil phase, the oil phase being in the form of stable droplets in a droplet layer at the bottom of the aqueous phase.

Referring to the drawings in particular, the invention embodied in FIG. 1 comprises a body spray assembly generally designated 10 comprising a glass container 12 which has an upright position, shown in FIG. 1, and that is at least partly transparent but, in the preferred embodiment of the invention, is completely transparent, colorless and made of glass.

Container 12 comprises a liquid composition 14 and a manual spray pump mechanism generally designated 18. Spray mechanism 18 is advantageously a reservoir pump having a push button or actuator 20 with a spray nozzle 22 for emitting a spray of liquid composition, a conduit neck 24 which extends down into a pump section 26 and a cup which is upwardly open and forms the reservoir of the reservoir pump. Reservoir pump 18 is commercially available from Valois of America in Greenwich, Conn. The pump has no dip tube, but instead sprays liquid that has been brought up into the upwardly open reservoir cup 28 by shaking or inverting the container 12. The reservoir cup forms supply means for the manual spray pump mechanism. This shaking operation is also necessary in accordance with the present invention to disperse the oil phase into the aqueous phase so an emulsion of both phases is sprayed from nozzle 22 when actuator 20 is pushed.

If the assembly is allowed to remain in the upright position of FIG. 1, the oil phase immediately begins to form visible droplets into a droplet layer 30 of stable spheres or droplets 32 which have a relatively narrow and well defined range of diameters (about 1 to 10 mm) and have the appearance of small white translucent pearls due to the use of a particular pigment combination. This appearance is enhanced by the fact that the outer surfaces of the outer spheres or droplets in the layers appear to press against the inner surface of the glass container, producing a slight flattening or dimpled surface which catches light differently from the remainder of the sphere, enhancing the shimmering, pearl-like appearance. Above layer 30, the aqueous phase of the composition 14 eventually becomes substantially clear and has a pale color or is colorless, producing a very attractive assembly of high consumer interest.

Figure 2:
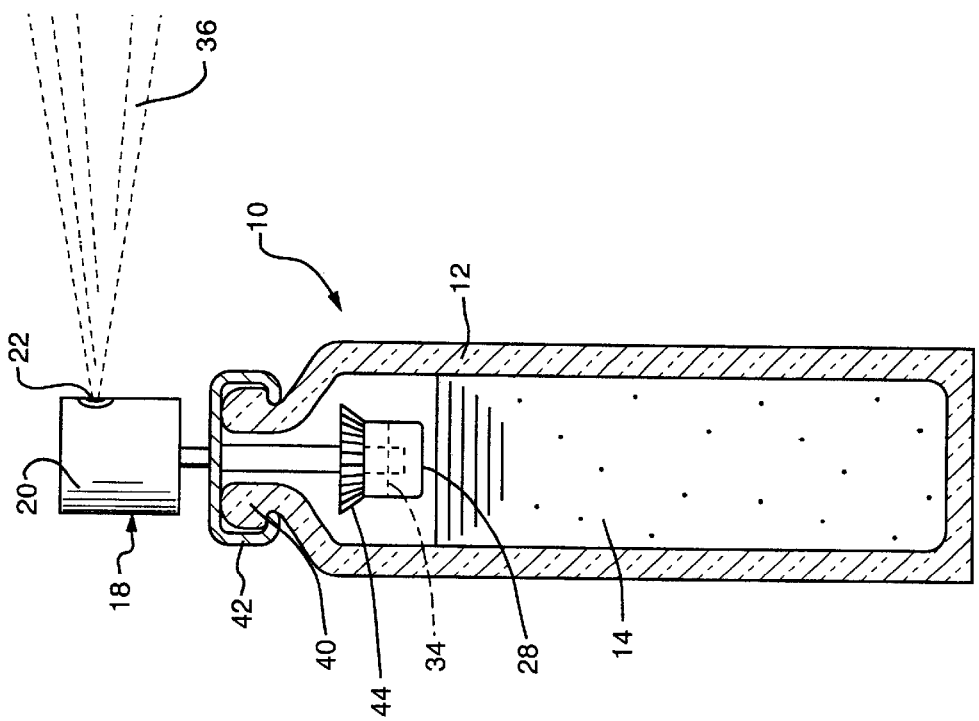
FIG. 2 is a view similar to FIG. 1, after the composition has been shaken up to disperse the oil-phase into the aqueous phase and, at the same, supply a charge of mixed composition into a reservoir pump used in accordance with the present invention for spraying the composition from the container.

FIG. 2 illustrates the assembly 10 after it has been vigorously shaken to disperse the droplets of oil into the aqueous phase to form the composition 14 into an emulsion. By this shaking, a level of composition at 34 is displaced into the reservoir 28 ready to be sprayed from nozzle 22 in the form of a spray pattern 36 when actuator 20 is depressed.

Spraying can continue until the liquid in reservoir 28 is depleted. Reservoir 28 is large enough to produce enough spray 36 for a reasonable application. If a user wishes more composition, the container 30 is simply shaken again or inverted to displace additional composition into the reservoir 28.

To avoid evaporation of volatile components and to avoid spillage, spray mechanism 18 is permanently fixed to the enlarged neck 40 of glass bottle 12 by use of a metal cap 42 having a lower rim crimped around a small diameter portion of neck 40. Evaporation of the volatile components would adversely effect the balance of the formulation, thus distorting the visual appearance of the pearls.

One feature of reservoir pump 18 is the inclusion of outwardly inclined spaced apart fins 44 which form a perimeter at the upper edge of the opening of reservoir 28 to help channel composition 14 into the reservoir where the composition is sloshed and splashed into the vicinity of reservoir 28, as the container 12 is shaken.

Figure 4:
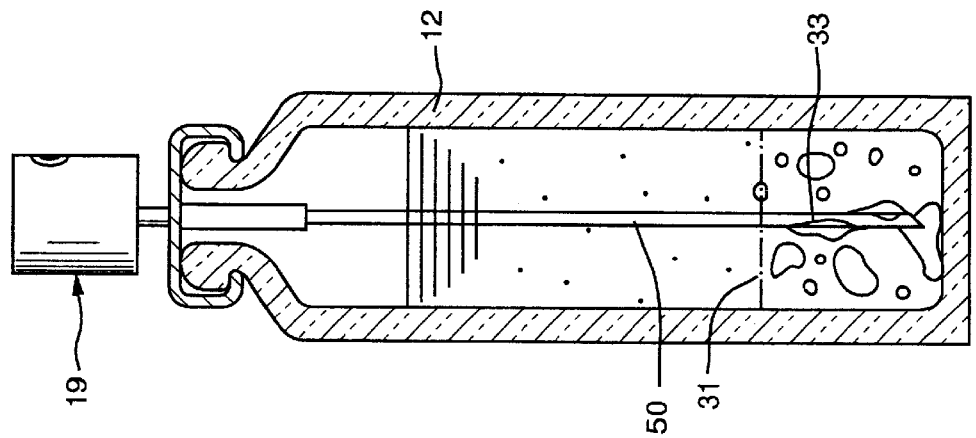
FIG. 4 is a view similar to FIG. 1, showing the results of utilizing a dip tube of conventional length which extends into the oil droplet layer but deforms or destroys the stable droplets in this layer.

Turning now to FIG. 4, the inventors have found that if a spray mechanism generally designated 19 of a conventional type having a long dip tube 50 extending partly or entirely into the oil droplet layer, shown by phantom line 31, it has the effect of disrupting the droplets, causing them to rupture, deform, smear and spread around the surface of the plastic dip tube at 33. The pearl-like droplets and the advantages of this attractive feature are lost and the appearance is further marred by the presence of the unsightly dip tube 50. The usual material of the dip tube is plastic, usually polyethylene (PE).

Figure 3:
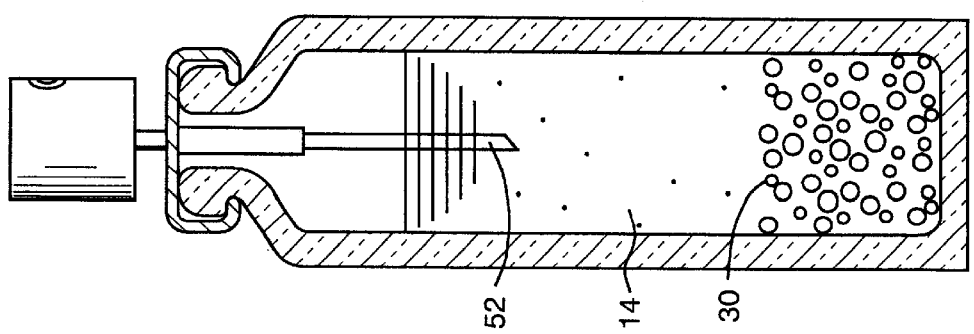
FIG. 3 is a view similar to FIG. 1, of another embodiment of the invention which utilizes a short dip tube in a manual pump for discharging the composition.

FIG. 3 illustrates another embodiment of the invention which utilizes a stubby dip tube 52 that extends into composition 14 but stops short of the droplet layer 30 to avoid the disadvantages of disrupting the droplets in the droplet layer. Tube 52 in FIG. 3 is the supply means for the manual pump. While less advantageous than the embodiment of FIG. 1 since all of the composition 14 can not be used, this illustrates an alternate embodiment of the invention which still uses a dip tube, but which utilizes spray means that are free of plastic parts that extend into the droplet layer.
Plastic in Contact With Droplet Layer:

Experiments were conducted determine what type of plastic caused damage to the otherwise stable droplets. These experiments also revealed that other ingredients of the liquid composition may be adversely effected by plastic in contact with the droplet layer. It was found, for example, that mica in the composition would cling to certain plastics.

The following table summarizes the results.

| Plastic | Composition Lab No. | Results |
|---|---|---|
| Urea | P26-JES-006-A | No apparent deformities of the pearl |
| Borax | P26-JES-006-D | No apparent deformities of the pearl |
| HDPE Fluorinated | P26-JES-006-F | No apparent deformities of the pearl |
| EVOH (Ethyl Vinyl Alcohol) | P26-JES-009-A | No apparent deformities of the pearl |
| GG9113PVC | P26-JES-008-A | No apparent deformities of the pearl |
| B155-Nylon-G | P26-JES-008-E | No apparent deformities of the pearl but the pearl clings to the piece of plastic |
| PVC (Polyvinyl) | P26-JES-006-E | No apparent deformities of the pearl but there are pigmentless oil drops attached to the piece of plastic |
| PET (Polyester) | P26-JES-007-A | No apparent deformities of the pearl but there are pigmentless oil drops attached to the piece of plastic |

-continued

| Plastic | Composition Lab No. | Results |
|---|---|---|
| GPS (General Polystyrene) | P26-JES-007-D | No apparent deformities of the pearl but there are pigmentless oil drops attached to the piece of plastic |
| G21 Anphorous Nylon | P26-JES-009-B | No apparent deformities of the pearl but there are pigmentless oil drops attached to the piece of plastic |
| HDPP (High Density Polypropylene) | P26-JES-006-B | No apparent deformities of the pearl but makes mica layer cling to the plastic. |
| HDPE (High Density Polyethylene) | P26-JES-006-C | No apparent deformities of the pearl but makes mica layer cling to the plastic. |
| LDPE (Low Density Polyethylene) | P26-JES-007-C | No apparent deformities of the pearl but makes mica layer cling to the plastic. |
| MPDE | P26-JES-007-D | No apparent deformities of the pearl but makes mica layer cling to the plastic. |
| ABS (Acrylonitrile Butadiene Styrene) | P26-JES-007-F | No apparent deformities of the pearl but makes mica layer cling to the plastic |
| Cyclo-olefin Copolymer | P26-JES-007-B | Pearls are deformed and cling to plastic in sheets, the product has permeated the plastic |
| 100% C-100 LLDPE | P26-JES-008-B | Pearls are deformed and cling to plastic in sheets |
| 58G High Gloss High Density PE | P26-JES-008-C | Pearls are deformed and cling to plastic in sheets |
| C-100 LLDPE W/ampact fluorolation process aide | P26-JES-008-D | Pearls are deformed and cling to plastic in sheets |
| C-100 LLDPE W/silicone | P26-JES-008-F | Pearls are deformed and cling to plastic in sheets |

Composition Formulae:

The following table lists the preferred ingredients of the composition. The aqueous phase automatically separates from the oil phase after a time, the oil phase settling into a layer of stable spheres or droplets.

| INCI NAME | TRADE NAME | % Range |
|---|---|---|
| Mineral Oil | Carnation White Mineral Oil | 10.00–30.00 |
| Mica (and) Titanium Dioxide | Flamengo Ultra Silk 2500 | 0.03–2.5 |
| Mica (and) Lauryl Lysine | Meralmica SVA | 0.004–1.0 |
| Water | Water | 10.00–20.00 |
| Butylene Glycol | 1,3 Butylene Glycol | 0.5–5 |
| Fragrance | Essential Oils* | 1.0–5.0 |
| SD Alcohol 40-B | SD Alcohol 40-B | 55.00–80.00 |

*Essential oils are fragrances without solubilizers such as stabilizers, surfactants or other additives. This type of ingredient is currently available and can be supplied by fragrance houses in the field.

| SUPPLIER | INCI NAME | TRADE NAME |
|---|---|---|
| Witco | Mineral Oil | Carnation White Mineral Oil |
| Engelhardt | Mica (and) Titanium Dioxide | Flamengo Ultra Silk 2500 |
| Engelhardt | Mica (and) Lauryl Lysine | Mearlmica SVA |
| Universal | Butylene Glycol | 1,3, Butylene Glycol |
| Union Carbide Different Suppliers | SD Alcohol 40-B Fragrance | SD Alcohol 40-B Fragrance |

The following table explains the purpose of each ingredient in the composition.

| INCI NAME | TRADE NAME | FUNCTION |
|---|---|---|
| Mineral Oil | Carnation White Mineral Oil | Contributes to the amount of pearls produced. The lower amount of Mineral Oil the fewer beads produced. Mineral Oil provides moisturization. |
| Mica (and) Titanium Dioxide | Flamengo Ultra Silk 2500 | The pigment is a critical part to the formation and size of pearl formed. The more pigment added the smaller the pearl will be. |
| Mica (and) Lauryl Lysine | Meralmica SVA | The pigment contributes to the size of pearl formed. The more pigment added the smaller the pearl will be. |
| Water | Water | Plays a part in the formation and retention of the pearl. If there is to much or to little water, the pearls are deformed. Also if there is to much water the pearls will float to the top. |
| Butylene Glycol | 1,3-Butylene Glycol | Plays a part in the formation and retention of the pearl. If there is to much or to little Butylene Glycol, the pearls will be deformed. Also if there is to much Butylene Glycol the pearls will float to the top. |
| Fragrance | Fragrance | Contributes to the smell of the product. |
| SD Alcohol 40-B | SD Alcohol 40-B | Helps keep the pearls on the bottom and also plays a part in the formation and retention of the pearl. If there is not enough alcohol in the system the pearls will not form or if they do form they will float to the top. This also acts as a preservative for the product. |

Some of the ingredients also interact in a favorable way according to the invention. There is a relationship between the mineral oil and the pigments. The ratio of these ingredients have an affect on the size of the pearls. For example when one increases the percentage of mineral oil and pigment, the size of the pearls are increased.

Two specific examples of the composition, identified as P18-JES-090 (low oil content) and P24-JES-075-A (high oil content), are given here, with manufacturing steps.

Lab Formula P 18-JES-090

| % W/W | Ingredient | INCI Name |
|---|---|---|
| PART A | | |
| 0.045 | Flamengo Ultra Silk 2500 | Mica (and) Titanium Dioxide |
| 0.005 | Mearlmica SVA | Mica (and) Lauryl Lysine |
| PART B | | |
| 14.000 | Carnation White Mineral Oil | Mineral Oil |
| PART C | | |
| 13.989 | Water | Water |

| % W/W | Ingredient | INCI Name |
|---|---|---|
| | PART D | |
| 1.000 | 1,3 Butylene Glycol | Butylene Glycol |
| 2.000 | Moonlight Path 3768-AY Mod 6 | Fragrance |
| | PART E | |
| 68.950 | SD Alcohol 40-B | SD Alcohol 40-B |
| 0.009 | Red 33 (1.0) | Red 33 |
| 0.002 | Blue 1 (1.0) | Blue 1 |
| 100.000 | Total | |

The droplets are glossy pearls that are about 1 to 6 mm. in diameter.

Lab Formula P24-JES-075-A

| % W/W | Ingredient | INCI Name |
|---|---|---|
| | PART A | |
| 0.081 | Flamengo Ultra Silk 2500 | Mica (and) Titanium Dioxide |
| 0.009 | Mearlmica SVA | Mica (and) Lauryl Lysine |
| | PART B | |
| 25.167 | Carnation White Mineral Oil | Mineral Oil |
| | PART C | |
| 12.139 | Water | Water |
| | PART D | |
| 0.900 | 1,3 Butylene Glycol | Butylene Glycol |
| 2.000 | Moonlight Path 3768-AY Mod 6 | Fragrance |
| | PART E | |
| 59.693 | SD Alcohol 40-B | SD Alcohol 40-B |
| 0.009 | Red 33 (1.0) | Red 33 |
| 0.002 | Blue 1 (1.0) | Blue 1 |
| 100.000 | Total | |

The droplets are glossy pearls about 1 to 8 mm. in diameter.

Lab Formula: P18-JES-090

Manufacturing Directions

Special Instructions

All equipment used in this process must be thoroughly cleaned and inspected. After the equipment is inspected and passed, an alcohol rinse is required.

PART A
 Step 1:
 Add ingredients together in a blender and blend for 20 minutes

PART B
 Step 1
 Add the mineral oil. Start propeller agitation at 1000 rpm.
 Step 2
 Slowly sprinkle in the Part A pigment blend/
 Step 3
 Mix for 5 minutes.

PART C
 Step 1
 Add the water to the Part B kettle
 Step 2
 Mix for 5 minutes with propeller agitator at 200 rpm.

PART D
 Step 1
 In a separate container, mix Part D for 5 minutes.
 Step 2
 Take Part D and add to Part B kettle
 Step 3
 Mix for 5 minutes with propeller agitator at 200 rpm.

PART E
 Special Instructions
 At the start of this step, the kettle must be sealed and kept sealed until all product is emptied from the kettle.
 Step 1
 Add the alcohol to the Part B kettle
 Step 2
 Mix for 5 minutes with propeller agitator at 200 rpm.
 Step 3
 Continue with the agitation. Take a sample of the batch to QC to determine the amount of color needed.
 Step 4
 Add the amount of color needed and mix until uniform. Submit to QC for analysis and approval.

Lab Formula: P24-JES-075-A

Manufacturing Directions

Special Instructions

All equipment used in this process must be thoroughly cleaned and inspected. After the equipment is inspected and passed, an alcohol rinse is required.

PART A
 Step 1
 Add ingredients together in a blender and blend for 20 minutes.

PART B
 Step 1
 Add the mineral oil. Start propeller agitation at 1000 rpm.
 Step 2
 Slowly sprinkle in the Part A pigment blend.
 Step 3
 Mix for 5 minutes.

PART C
 Step 1
 Add the water to the Part B kettle.
 Step 2
 Mix for 5 minutes with propeller agitator at 200 rpm.

PART D
 Step 1
 In a separate container, mix Part D for 5 minutes.
 Step 2
 Take Part D and add to Part B kettle.
 Step 3
 Mix for 5 minutes with propeller agitator at 200 rpm.

PART E
 Special Instructions
 At the start of this step, the kettle must be sealed and kept sealed until all product is emptied from the kettle.
 Step 1
 Add the alcohol to the Part B kettle.
 Step 2
 Mix for 5 minutes with propeller agitator at 200 rpm.
 Step 3
 Continue with the agitation. Take a sample of the batch to QC to determine the amount of color needed.
 Step 4
 Add the amount of color needed, and mix until uniform. Submit to QC for analysis and approval.

Acidic Ingredients With Fragranced Moisturizing Pearls:
 The effect of acidity was also investigated.

Most of the composition formulas have a pH of 7.8. It is assumed that previous products also have a pH in this range. Another aim of the invention is to lower the pH of the product to levels between 3.0–7.0.

The following types of acidic ingredients were used. These were Lactic Acid, Dihydroxyacetone, Citric Acid and Hydrochloric Acid. These ingredients were added at a range of 0.5% to 5.0%. The resulting pH's had a range of 3.0–5.5. Pearls in the samples with dihydroxyacetone above 2% began to float. The pearls or droplets that floated retained the round pearl shape. Additional alcohol was added to make the pearls sink. Samples with Lactic and/or Citric Acid above 1% had distorted pearls that floated on the top of the composition in its container. All other samples retained the round pearl shape formation and stayed on the bottom, the preferred form of the invention.

It was surprising that the hydrogen ion concentration could be reduced by many fold (pH 7 to pH 3) without damaging the appearance of the pearls. This was surprising because changes in other ingredients of the composition caused drastic changes in the formation and/or appearance of the oil droplets or pearls.

Selection of Fragrance:

A proper selection of fragrance type is also important for the invention. It was found that substantially pure fragrance oil, without solubilizers such as surfactants or other like ingredients, worked best. It was found that using standard fragrances with the usual solubilizers caused loss of stability, shape or adequate size in the pearls or droplets.

The following table illustrates the results of some of the tests that were conducted.

| Fragrance | Mod No. | Results |
| --- | --- | --- |
| Juniper Breeze | TCB44327 | Formed broken spheres |
| Raspberry | WF122298 | Non-round spheres |
| Pearberry | 5315-AY | Small round spheres |
| Flower Walk | 5111-BA | Round sphere |
| Moonlight Path | 3768-AY Mod 6 | Round sphere |
| Calming Waters | 5087-BA | Round sphere |
| Stolen Moments | 1923-BC | Round sphere |
| Dream Fields | 143.604-L | Wrinkled broken pieces |
| Morning Song | 4431011 | Wrinkled broken pieces |
| Garden Glow | Version A | Round, elongated wrinkled spheres |
| Garden Glow | Version B | Round, elongated wrinkled spheres |
| Garden Glow | Version C | Round, elongated wrinkled spheres |

The present invention can also be used to apply various oily and/or aqueous active ingredients to the skin, while still retaining the attractive "pearls" and avoiding the unsightly pump dip tube.

UV Absorber With Fragranced Moisturizing Pearls:

The inventors first experimented with Benzophenone-4 in their formulas. The amount added ranged from 0.01–0.05%. They found that Benzophenone-4 adversely affected the pearl stability, and did not protect the color from fading.

Samples of the water and organic solvents with water-soluble colors were made. To these samples, Benzophenone-1, Benzophenone-3, and Benzophenone-4 were added. The Benzophenone-4 samples stripped the color out in both UV and Dark conditions. The Benzophenone-1 and Benzophenone-3 retained the original colors.

Further experiments with Benzophenone-3 at 0.05% in the completed formulation produced positive results with no fading of color or distortion of the pearls.

Vitamin Additives:

Oil soluble vitamins and other oil soluble materials would reside in the lipophilic oil portion of the formulation. Water soluble vitamins and other water soluble materials would reside in the hydrophilic portion of the formulation.

| Vitamin | Lab No. | Results |
| --- | --- | --- |
| Beta-Carotene 0.01% | P24-JES-098-A | Pearls enlarged and were rust color |
| Beta-Carotene 0.05% | P24-JES-098-B | Pearls enlarged and were rust color |
| Retinol 0.01% | P24-JES-099-A | Pearls a little bit larger |
| Retinol 0.05% | P24-JES-099-B | Pearls a little bit larger |
| Vitamin E 0.01% | P26-JES-001-A | Solution is a little hazy. Pearls stable |
| Vitamin E 0.05% | P26-JES-001-B | Solution is a little hazy. Pearls stable |
| Panthenol 0.01% | P26-JES-002-A | Pearls stable |
| Panthenol 0.05% | P26-JES-002-B | Pearls stable |
| Ascorbic Acid 0.01% | P26-JES-003-A | Solution became slightly hazier and pearls enlarged at this concentration of ascorbic acid |
| Ascorbic Acid 0.05% | P26-JES-003-B | The haziness of the solution and the enlargement of the pearls further increased rleative to that of 0.01% |
| All of the above added with citric but without Beta-Carotene | P26-JES-010-A | Solution is hazier. pH is 3.05. Pearls stable |

Comparison With Other Compositions:

In the following table the typical composition of the invention (center column) is compared to the compositions of the Yves Rocher product and the Shiseido Patent.

| Yves Rocher | Invention | Shiseido Patent |
| --- | --- | --- |
| Alcohol | Alcohol | OILS |
| Mineral Oil C11–12 Isoparaffin | Mineral Oil | High molecular Weight hydrocarbons ie: liquid paraffin, scalene |
| Water | Water | |
| Fragrance | Fragrance | Mono or Di-esters of fatty acids |
| Sage Extract | | |
| Glycerin | | Vegetable and animal oils |
| Streptomyces Extract | | |
| Sodium PCT | | High fatty acids having 10 to 25 carbon atoms |
| Urea | | |
| Sage Oil | | Fatty alcohols having 10 to 25 carbon atoms. |
| Peppermint Oil | | |
| Propylene Glycol | Butylene Glycol | Synthetic Oils |
| Mica | Mica | all can be used alone or in combination |
| Titanium Dioxide | Titanium Dioxide | |
| Colors | Colors | PIGMENTS |
| | | Anhydrous Silic Acid |
| | | Calcium aluminate |
| | | Calcium carbonate |
| | | Titanium Dioxide |
| | | Zinc |
| | | Zinc peroxide |
| | | Talc |
| | | Colloidal Kaolin |
| | | Inorganic pearl agent |
| | | Bentonic |
| | | Alumine |
| | | Pearl |

-continued

| Yves Rocher | Invention | Shiseido Patent |
|---|---|---|
| | | Antimony oxide |
| | | Magnesium silicate |
| | | Yellow iron oxide |
| | | Black iron oxide |
| | | Bismuth oxychloride |
| | | Zinc Laurate |
| | | Microcrystalline cellulose |
| | | Nylon 12 |
| | | Permeant orange |
| | | Carbon black |
| | | Lithol Rubin BCA |
| | | Polyvinyl chloride |
| | | mica |
| | | LIQUIDS |
| | | Organic liquids that are completely immiscible |
| | | or slightly immiscible in oil. Has a specific |
| | | gravity of less than 1 |
| | | ie: monohydric alcohol having carbon atoms |
| | | of no greater than 5. Polyhydric alcohols |
| | | having carbon atoms of no greater than 6 |
| | | Polyethylene glycol, ethers, ketones. |
| | | Water |
| | | Mentions various additives: colorants antioxidants perfumes, uv abosrbers antiseptic wetting agents etc. |

While a specific embodiment of the invention has been shown and described in detail to illustrate the application of the principles of the invention, it will be understood that the invention may be embodied otherwise without departing from such principles.

What is claimed is:

1. A body spray assembly comprising:
   a container which has an upright position and that is at least partly transparent;
   a liquid composition in the container; and
   spray means connected to the container for spraying the liquid composition from the container;
   the composition including an oil phase, an aqueous phase and pigment in the form of particles which are effective to form the oil phase into stable droplets that remain in a droplet layer in the aqueous phase after the composition is allowed to stand for a period of time, the droplets being at least partly visible in the container;
   the spray means being free of any parts that extend into the droplet layer when the container is in its upright position to avoid rupturing the stable droplets by contact with any parts.

2. An assembly according to claim 1, wherein the spray means comprises a manual pump having supply means for supplying liquid to the manual pump, no portion the supply means extending into the droplet layer.

3. An assembly according to claim 2, wherein the oil phase includes fragrance which is free of solubilizers.

4. An assembly according to claim 2, wherein the spray means comprises a manual reservoir pump.

5. An assembly according to claim 2, wherein the oil phase is about 10 to 30 wt % of the liquid composition, the aqueous phase including about 55 to 80 wt % of the composition alcohol, the pigment being about 0.03 to 4 wt % of the composition and including mica and a substantially pure fragrance in the form of essential oil in the oil phase which is substantially free of solubilizer and is present in the composition in an amount of up to about 5 wt %.

6. An assembly according to claim 2, wherein the oil phase includes mineral oil, the pigment comprises at least one of mica, titanium dioxide and lauryl lysine.

7. An assembly according to claim 5, wherein the composition comprises between 2 and 5 wt % fragrance.

8. An assembly according to claim 5, wherein the manual pump is a reservoir pump that is sealed to the container.

9. An assembly according to claim 5, wherein the composition comprises about: 10.00–30.00 wt % mineral oil; 0.03–2.5 wt % mica with titanium dioxide; 0.004–1.0 wt % mica with lauryl lysine; 10.00–20.00 wt % water; 0.5–5 wt % butylene glycol; 1.0–5.0 fragrance; and 55.00–80.00 wt % SD alcohol 40-B.

10. An assembly according to claim 2, including at least one vitamin additive.

11. An assembly according to claim 10, wherein the vitamin additive is an oil in the oil phase.

12. An assembly according to claim 2, including at least one acid in the composition for adjusting the composition pH to about 3–7 pH.

13. An assembly according to claim 12, wherein the pH range is 3–6.5 pH.

14. An assembly according to claim 12, wherein the composition includes up to 30 wt % acid.

15. An assembly according to claim 14, including about 1–5 wt % acid.

16. An assembly according to claim 14, wherein the acid is an organic acid.

17. An assembly according to claim 16, wherein the acid is an alpha- or beta-hydroxy acid.

18. An assembly according to claim 12, wherein the acid comprises hydroxy carboxylic acid.

19. An assembly according to claim 2, wherein the pump is permanently sealed to the container.

20. An assembly according to claim 2, wherein the oil phase comprises mineral oil and fragrance, the pigment comprises at least one of mica, titanium dioxide and lauryl lysine, and the aqueous phase including water, butylene glycol and alcohol.

21. An assembly according to claim 2, wherein the supply means comprises an upwardly open reservoir cup which is above a level of the liquid composition in the container in the upright position of the container.

22. An assembly according to claim 2, wherein the supply means comprises a stub tube, the stub tube extending into the composition above the droplet layer.

* * * * *